(12) United States Patent
Doe et al.

(10) Patent No.: US 7,137,290 B2
(45) Date of Patent: Nov. 21, 2006

(54) ROTARY RHEOMETER MAGNETIC BEARING

(75) Inventors: Nigel Doe, Horsham (GB); Peter Foster, Lingfield (GB)

(73) Assignee: Waters Investment Limited, New Castle, DE (US)

( * ) Notice: Subject to any disclaimer, the term of this patent is extended or adjusted under 35 U.S.C. 154(b) by 0 days.

(21) Appl. No.: 11/364,342

(22) Filed: Mar. 1, 2006

(65) Prior Publication Data

US 2006/0144128 A1    Jul. 6, 2006

Related U.S. Application Data

(63) Continuation of application No. 11/075,414, filed on Mar. 9, 2005, now Pat. No. 7,017,393.

(60) Provisional application No. 60/551,802, filed on Mar. 11, 2004.

(51) Int. Cl.
    *G01N 11/14* (2006.01)
(52) U.S. Cl. .................................................. 73/54.35
(58) Field of Classification Search ............... 73/54.35, 73/54.23; 310/46
    See application file for complete search history.

(56) References Cited

U.S. PATENT DOCUMENTS

| | | | |
|---|---|---|---|
| 4,524,611 A | 6/1986 | Richon et al. ............. 73/54.35 |
| 4,630,468 A | 12/1986 | Sweet ........................ 73/54.43 |
| 4,878,377 A | 11/1989 | Abel .......................... 73/54.32 |
| 5,142,175 A * | 8/1992 | Watanabe .................. 310/90.5 |
| 5,777,212 A | 7/1998 | Sekiguchi et al. ......... 73/54.33 |
| 6,218,751 B1 | 4/2001 | Bohlin ....................... 310/90.5 |
| 6,359,357 B1 * | 3/2002 | Blumenstock ............. 310/90.5 |
| 6,572,610 B1 | 6/2003 | Kovalcheck et al. .......... 606/21 |

OTHER PUBLICATIONS

Don Palazek "Magnetic Bearing Torsional Crepp Apparatus" Journal of Polymer Science, A2 6:621-638.
International Search Report and Written Opinion.

* cited by examiner

*Primary Examiner*—Daniel S. Larkin
*Assistant Examiner*—Tamiko Bellamy
(74) *Attorney, Agent, or Firm*—Pillsbury Winthrop Shaw Pittman

(57) ABSTRACT

A rotary rheometer having a magnetic thrust bearing. The thrust disk of the magnetic thrust bearing being situated between a pair of magnetic actuator assemblies and extending beyond the circumference of the actuator assemblies so as to encompass the magnetic flux lines generated by the actuator assemblies, thus minimizing likelihood of an undesirable preferential position or side load.

20 Claims, 5 Drawing Sheets

ROTARY RHEOMETER MAGNETIC BEARING

This Application is a Continuation of and claims priority to U.S. Application Ser. No. 11/075,414 entitled Rotary Rheometer Magnetic Bearing, filed on Mar. 9, 2005 now U.S. Pat. No. 7,017,393, which claims the benefit of U.S. Provisional Application No. 60/551,802, filed Mar. 11, 2004.

BACKGROUND

1. Field of the Invention

The present invention relates generally to rheometers, which are used to characterize materials by measuring the materials' viscosity, elasticity, shear thinning, yield stress, compliance and/or other material properties.

2. Background of the Invention

Rotary rheometers, viscometers or viscosimeters are used to measure fluid or other properties of materials such as their viscosity by rotating, deflecting or oscillating a measuring object in a material, and measuring, for example, the torque required to rotate or deflect or oscillate the object within the material. As used herein, the term "rheometer" shall mean rheometers, viscometers, viscosimeters and similar instruments that are used to measure the properties of fluid or similar (see list below) materials.

The term "measuring object" shall mean an object having any one of several geometries, including, for example, cones, discs, vanes, parallel plates, concentric cylinders and double concentric cylinders. The materials may be liquids, oils, dispersions, suspensions, emulsions, adhesives, biological fluids such as blood, polymers, gels, pastes, slurries, melts, resins, powders or mixtures thereof. Such materials shall all be referred to generically as "fluids" herein. More specific examples of materials include asphalt, chocolate, drilling mud, lubricants, oils, greases, photoresists, liquid cements, elastomers, thermoplastics, thermosets and coatings.

As is known to one of ordinary skill in the art, many different geometries may be used for the measuring object in addition to the cylinders, cones, vanes and plates listed above. The measuring objects may be made of, for example, stainless steel, anodized aluminum or titanium. U.S. Pat. No. 5,777,212 to Sekiguchi et al., U.S. Pat. No. 4,878,377 to Abel and U.S. Pat. No. 4,630,468 to Sweet describe various configurations, constructions and applications of rheometers.

FIG. 1A is a schematic perspective view of a prior art rotary rheometer 100, showing lead screw 101, draw rod 102, optical encoder 103, air bearing 104, drive shaft 105, drag cup motor 106, measuring object 107 (shown in FIG. 1A as a parallel plate), heating/cooling assembly (e.g., a Peltier plate) 108, temperature sensor 110 (e.g., a Pt temperature sensor), surface 111, normal force transducer 112, and auto gap set motor and encoder 113. FIG. 1B is a schematic drawing of a concentric cylinder configuration in position on the rheometer of FIG. 1A, showing the control jacket 120 of the concentric cylinder configuration on top of normal force transducer 112 of rheometer 100. FIG. 1B shows a cylindrical measuring object 121 (used in this configuration instead of the parallel plate measuring object 107 shown in FIG. 1A.

Typical rheometers include essentially two types of bearings for maintaining the position of the shaft, radial bearings and thrust bearings. Modern rheometers utilize air (or other mechanical) bearings for both the thrust and radial bearings because they are non-contact and low friction. The viscosity of high-pressure air in the bearing is one of the limiting factors to the lowest torques that may be applied by the motor, while still resulting in accurate data. One such alternative would be to use a bearing that levitates magnetically.

In rheometers, magnetic bearings have not been fully commercialized. One magenetic bearing that has been utilized in rheometer applications was described by Don Plazek in 1968 ("Magnetic Bearing Torsional Creep Apparatus," Journal of Polymer Science, A2 6:621–638). This magnetic bearing utilized a combination thrust and radial bearing of a cone and ring shape. Such a magnetic bearing has alignment and preferential position issues and its design is not considered robust enough for typical laboratory use. In addition, this rheometer did not provide the full spectrum of capabilities of typical modern rheometers in that it could only be used to measure creep and was not suitable for other applications such as, for example, steady shear, dynamic and stress relaxation.

SUMMARY OF THE INVENTION

Magnetic bearings are well known in other areas, but there are particular requirements for a rotary rheometer. The bearing should not have a preferential position or apply a side load that could result in undesirably interactions with radial bearings. If the pole pieces of the electromagnets and thrust disk are exactly the same size and perfectly aligned, then the magnetic flux lines will cut vertically through the disk in a symmetrical manner. If, however, there is any misalignment or difference in size, a preferential position or side load can result. In order to overcome these issues, the present invention utilizes a thrust disk sized so as to be larger than the exterior and interior circumferences of the pole-pieces of the magnetic bearing. In this configuration, there is always thrust disk material for the magnetic flux lines to pass through, thus minimizing the likelihood of a preferential position or a side load.

The magnetic thrust bearing of embodiments of the present invention is disk shaped and may be used in conjunction with two separate radial bearings, for example radial air bearings, that impart a radial stiffness and robustness. It is believed that this configuration may open the use of magnetic thrust bearings to many more applications because of the robustness of the overall design and lower cost of manufacture.

DETAILED DESCRIPTION OF THE INVENTION

Figure 1A:
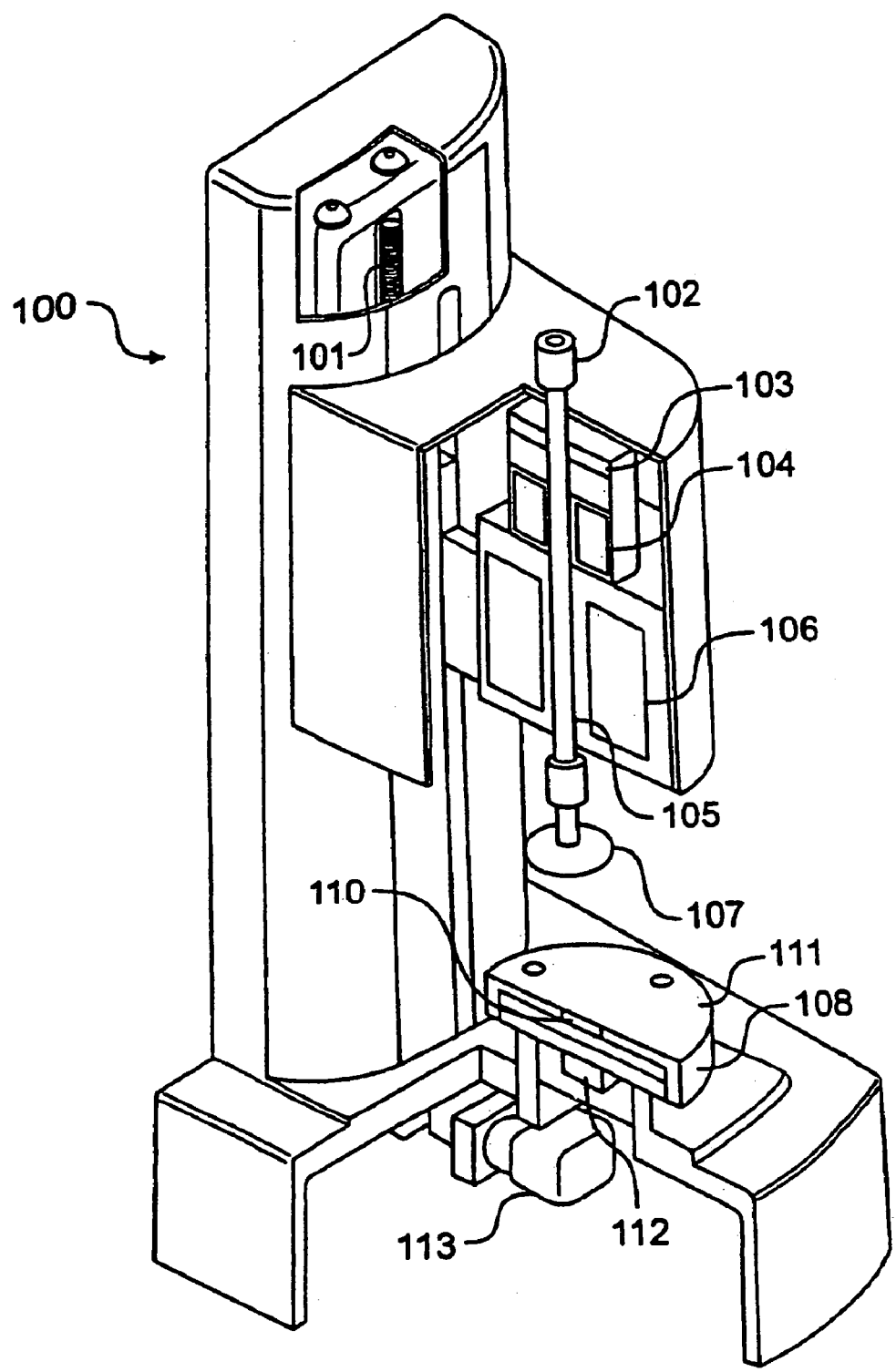
FIG. 1A is a schematic diagram of a perspective view of a prior art rotary rheometer.
Figure 1B:
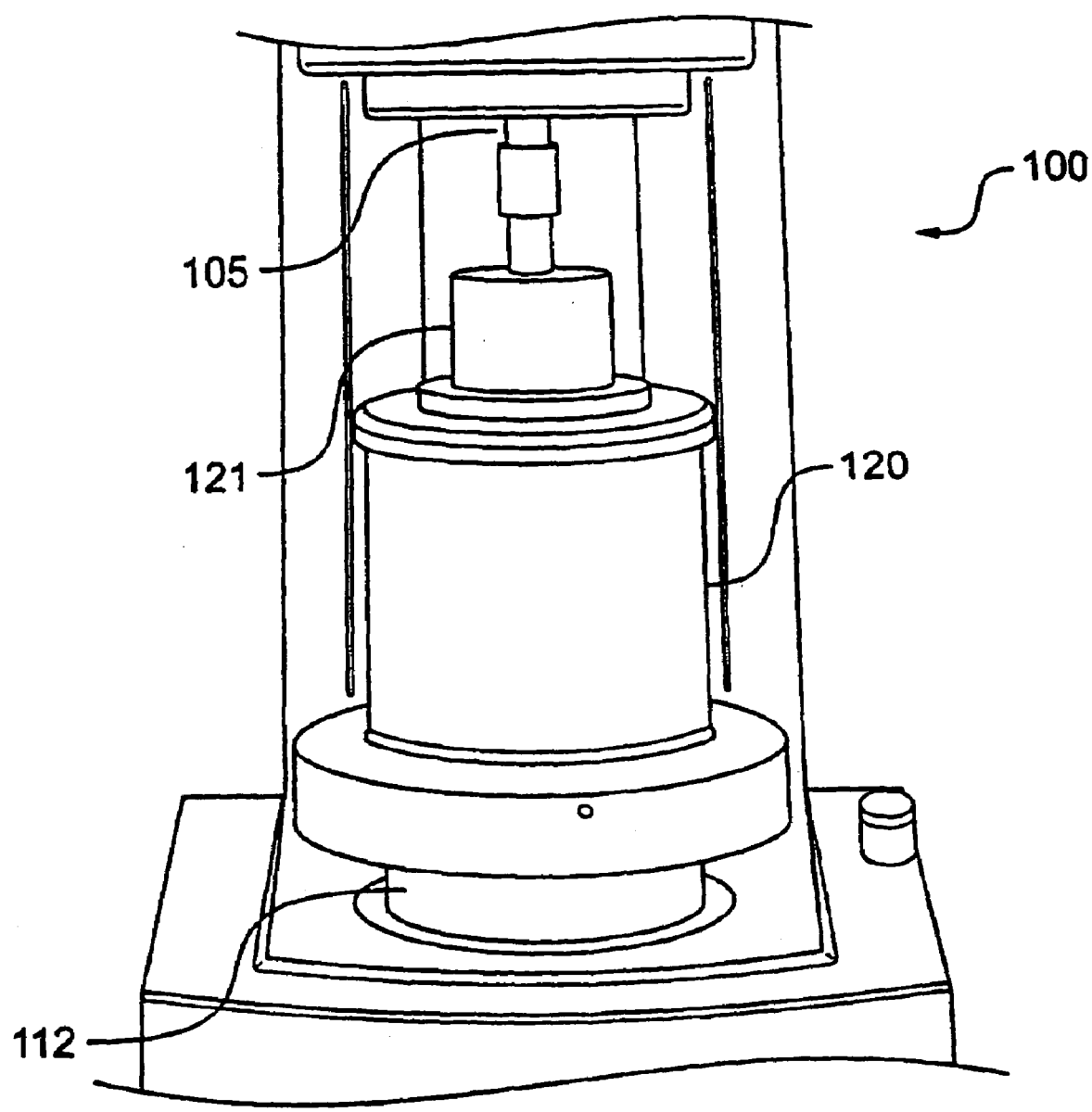
FIG. 1B is a schematic diagram of a concentric cylinder configuration in position on the rheometer of FIG. 1A.
Figure 2:
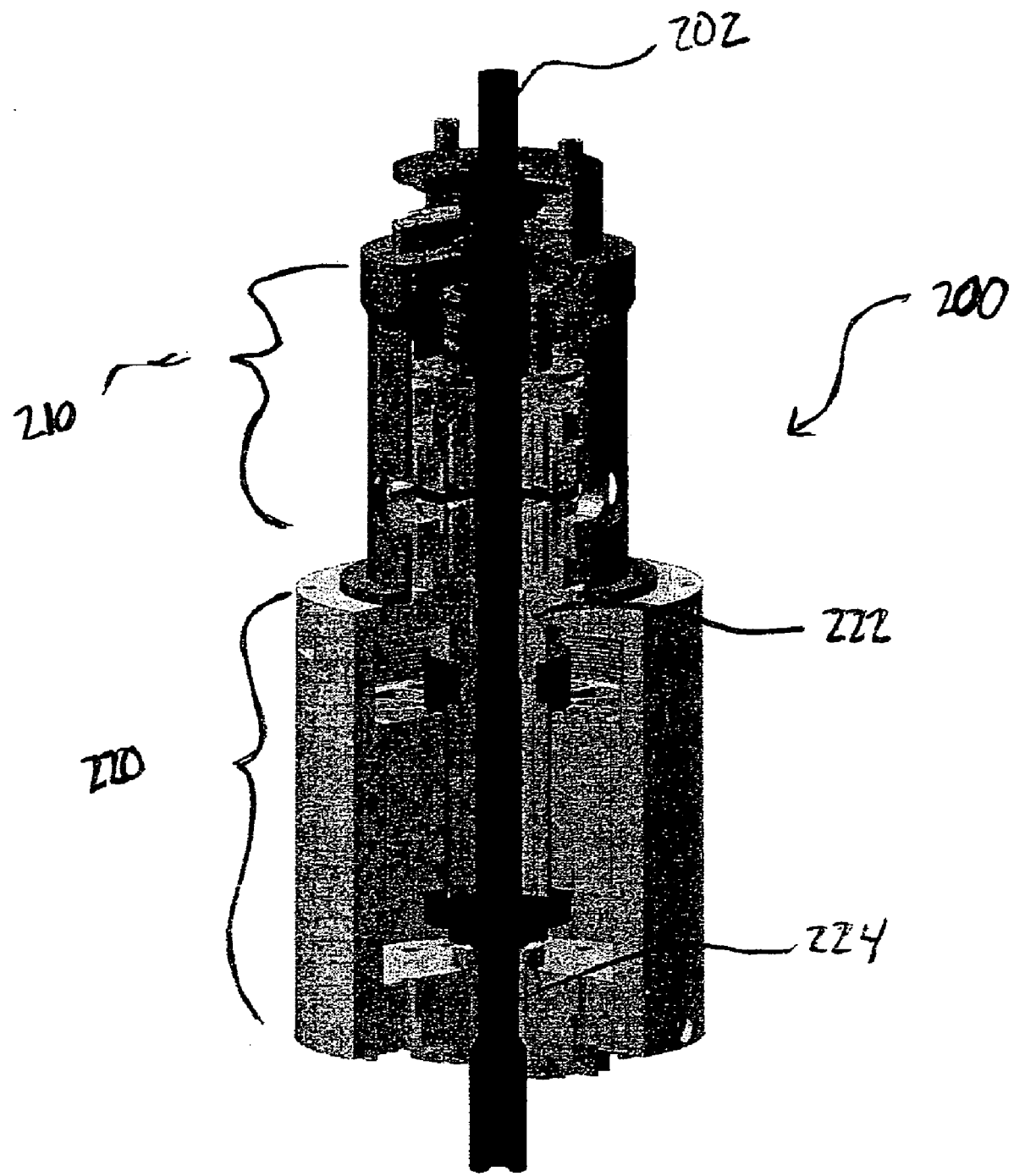
FIG. 2 is a schematic diagram of a perspective view of a rotary rheometer according to an exemplary embodiment of the present invention.

FIG. 2 is a perspective cut-away schematic diagram that shows an exemplary embodiment of a rheometer shaft housing 200 comprising a magnetic thrust bearing assembly 210 of the present invention. Housing 200 houses rotary shaft 202, which is rotated by motor assembly 220. Motor assembly 220 comprises a pair of radial bearings 222 and 224. Radial bearings 222 and 224 comprise conventional air bearings, but could comprise other mechanical bearings known in the art.

Figure 3:
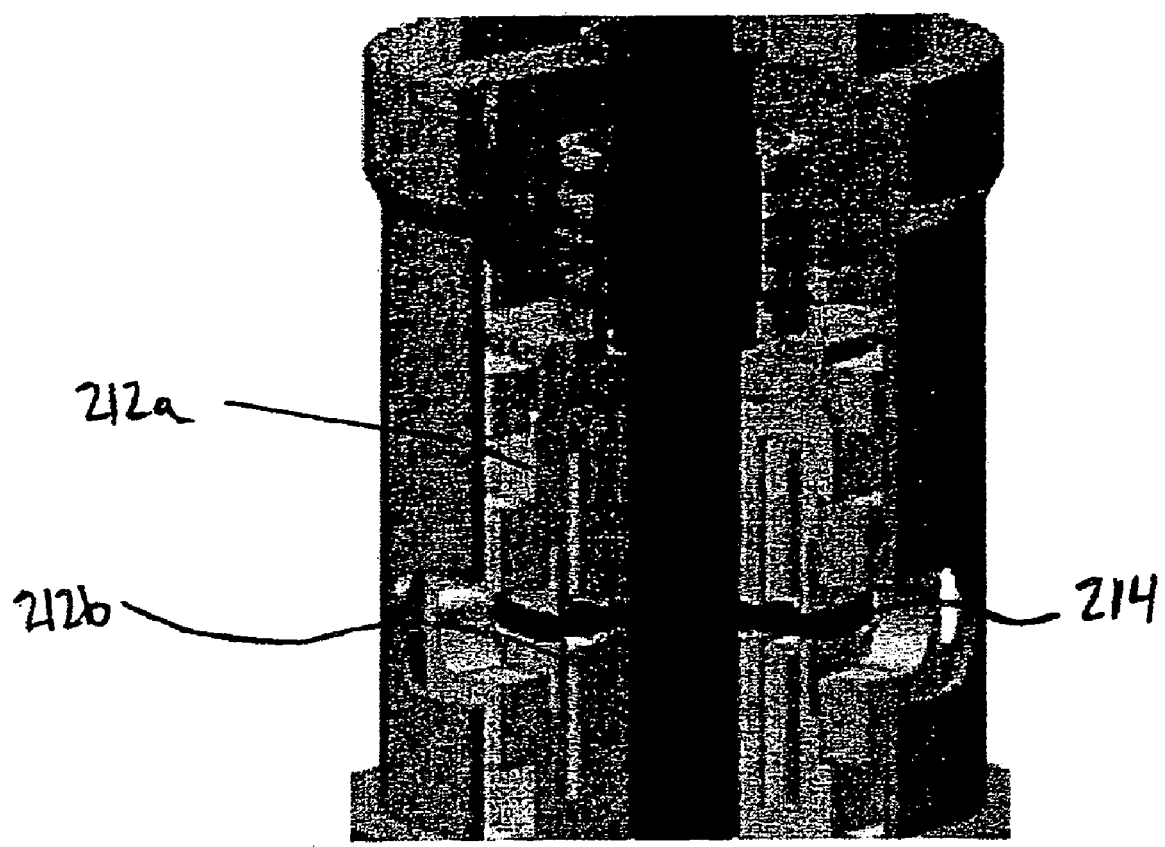
FIG. 3 is a schematic diagram of the upper portion of the rotary rheometer of FIG. 2.

In addition to radial bearings 222 and 224, housing 200 also comprises the thrust bearing assembly 210. Unlike conventional air or mechanical bearings, thrust bearing assembly 210 is a magnetic thrust bearing. As seen in FIG. 3, which is a zoomed in drawing of the thrust bearing assembly 210 depicted in FIG. 2, thrust bearing assembly 210 comprises a pair of magnetic actuator assemblies or magnets 212a and 212b. Between magnets 212a and 212b is situated thrust disk 214. Thrust disk 214 may be made of, for example, magnetic iron. In the embodiment shown, magnets 212a and 212b are attractive magnets and thus maintain the position of thrust disk 214 between them. This in turn maintains the vertical position of the shaft within motor housing 200.

Figure 4:
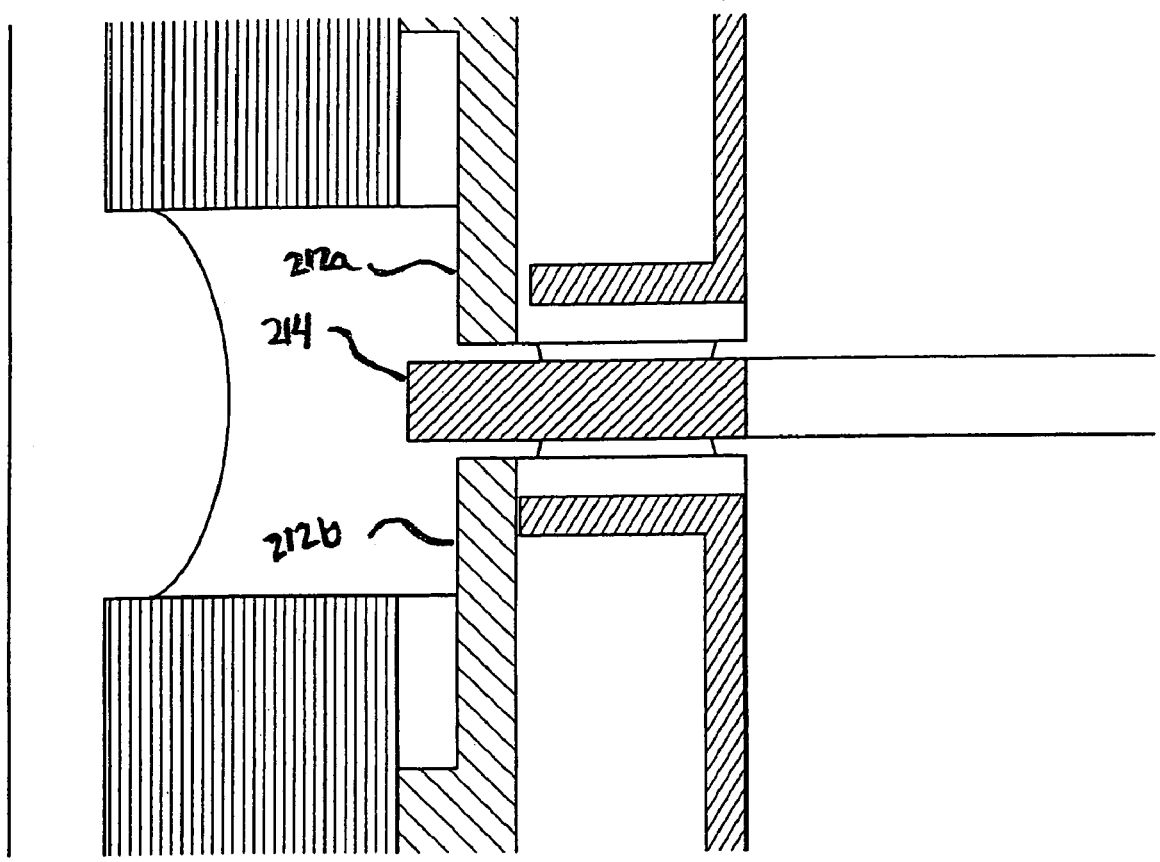
FIG. 4 is a partial cross section of the magnetic thrust bearing depicted in FIGS. 2 and 3.

As seen in FIG. 4, a partial cross-section of thrust bearing assembly 210, thrust disk 214 is larger than the two magnets 212a and 212b. This increased size allows substantially all of the magnetic flux lines to cut vertically through the disk. It may be possible to manufacture electromagnets so that they are exactly the same size as the thrust disks, but such a thrust disk would be nearly impossible to align and assemble, thus greatly increasing manufacturing and operational costs. Any such misalignment can result in an undesirable preferential position or sideload, thus requiring constant adjustment and/or recalibration.

Accordingly, thrust disk 214 is of a sufficient size so as to compensate for and always provide thrust disk material for the magnetic flux lines to pass through. This, in turn, minimizes the likelihood of a preferential position or sideload. One of skill in the art will understand that the proportions of the disk versus the magnets shown is only exemplary and is not to scale and that the thrust disk need only be of a sufficient size in comparison to the magnets to encompass the flux lines. Optimization of the magnet size versus disk size is also contemplated by the present invention so that torque performance can be maximized while still minimizing moment of inertia and maintaining proper axial, lateral, and torsional stiffness.

Other advantages that can be achieved by use of a magnetic thrust bearing over an air thrust bearing are that the bearing gap can be increased, for example, to approximately 0.5 mm on each side rather than the microns associated with an air bearing. The magnetic bearing also reduces friction and residual torque resulting in ultra-low usable torques. The magnetic thrust bearing is also more robust and less susceptible to contamination.

As an example of the improved characteristics, the following table shows comparative specifications of the AR-G2 rotary rheometer having the magnetic thrust bearing of the present invention versus the AR 2000 rotary rehometer (both manufactured by TA Instruments, Inc.) having conventional air bearings only. In the following chart, CR stands for controlled rate mode and CS stands for controlled stress mode:

| Specification | AR-G2 | AR 2000 |
|---|---|---|
| Minimum torque: oscillation CR | 0.003 µNm | 0.03 µNm |
| Minimum torque: oscillation CS | 0.003 µNm | 0.1 µNm |

-continued

| Specification | AR-G2 | AR 2000 |
|---|---|---|
| Minimum torque: steady shear CR | 0.01 µNm | 0.05 µNm |
| Minimum torque: steady shear CS | 0.01 µNm | 0.1 µNm |

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

What is claimed is:

1. A rheometer comprising:
   a rotary shaft;
   a motor assembly for rotating the rotary shaft, wherein the motor assembly comprises at least one radial bearing; and
   a magnetic thrust bearing having a thrust disk coaxial with the rotary shaft and positioned between two magnets, wherein the thrust disk is configured to allow substantially all of magnetic flux lines generated by the magnets to cut through the thrust disk.

2. The rheometer of claim 1, wherein an outer diameter of the thrust disk is of sufficient size to encompass the magnetic flux lines.

3. The rheometer of claim 1, wherein an outer diameter of the thrust disk is larger than an outer diameter of the magnets.

4. The rheometer of claim 1, wherein the magnets exert attractive force upon the thrust disk.

5. The rheometer of claim 1, wherein the at least one radial bearing comprises an air bearing.

6. The rheometer of claim 1, wherein a bearing gap between the thrust disk and at least one of the magnets is approximately 0.5 mm.

7. The rheometer of claim 1, wherein a bearing gap between the thrust disk and each of the magnets is approximately 0.5 mm.

8. The rheometer of claim 1, wherein the thrust disk comprises magnetic iron.

9. A magnetic thrust bearing for a rotary shaft, comprising:
   a pair of magnets; and
   a thrust disk coaxial with the rotary shaft and positioned between the pair of magnets,
   wherein the thrust disk is configured to allow substantially all of magnetic flux lines generated by the pair of magnets to cut through the thrust disk.

10. The magnetic thrust bearing of claim 9, wherein an outer diameter of the thrust disk is of sufficient size to encompass the magnetic flux lines.

11. The magnetic thrust bearing of claim 10, wherein an outer diameter of the thrust disk is of sufficient size to always encompass the magnetic flux lines.

12. The magnetic thrust bearing of claim 9, wherein an outer diameter of the thrust disk is larger than an outer diameter of the pair of magnets.

13. The magnetic thrust bearing of claim 9, wherein the pair of magnets exert attractive force upon the thrust disk.

14. The magnetic thrust bearing of claim 9, wherein a bearing gap between the thrust disk and at least one of the pair of magnets is approximately 0.5 mm.

15. The magnetic thrust bearing of claim 9, wherein a bearing gap between the thrust disk and each of the pair of magnets is approximately 0.5 mm.

16. A rotary motor, comprising:
   a rotary shaft;
   at least one radial bearing; and
   a magnetic thrust bearing comprising a thrust disk coaxial with the rotary shaft and positioned between two magnets, wherein the thrust disk is configured to allow substantially all of magnetic flux lines generated by the magnets to cut through the thrust disk.

17. The rotary motor of claim 16, wherein an outer diameter of the thrust disk is larger than an outer diameter of the two magnets.

18. The rotary motor of claim 16, wherein the outer diameter of the thrust disk is of sufficient size to always encompass the magnetic flux lines generated by the magnets.

19. The rotary motor of claim 16, wherein the magnets exert attractive force upon the magnetic disk.

20. The rotary motor of claim 16, wherein a bearing gap between the thrust disk and each of the magnets is approximately 0.5 mm.

* * * * *